United States Patent
Choe et al.

(10) Patent No.: US 11,214,643 B2
(45) Date of Patent: *Jan. 4, 2022

(54) MODIFICATION POLYMERIZATION INITIATOR AND METHOD FOR PREPARING THE SAME

(71) Applicant: LG Chem, Ltd., Seoul (KR)

(72) Inventors: Dong Cheol Choe, Daejeon (KR); Jae Hoon Choe, Daejeon (KR); Jung Yong Lee, Daejeon (KR); Hyeon Hui Kim, Daejeon (KR); Jong Young Choi, Daejeon (KR); Won Jae Lee, Daejeon (KR)

(73) Assignee: LG Chem, Ltd.

( * ) Notice: Subject to any disclaimer, the term of this patent is extended or adjusted under 35 U.S.C. 154(b) by 0 days.

This patent is subject to a terminal disclaimer.

(21) Appl. No.: 16/756,023

(22) PCT Filed: Jun. 19, 2019

(86) PCT No.: PCT/KR2019/007405
§ 371 (c)(1),
(2) Date: Apr. 14, 2020

(87) PCT Pub. No.: WO2019/245287
PCT Pub. Date: Dec. 26, 2019

(65) Prior Publication Data
US 2021/0147599 A1    May 20, 2021

(30) Foreign Application Priority Data

Jun. 20, 2018 (KR) .................. 10-2018-0070890
Jun. 20, 2018 (KR) .................. 10-2018-0070891

(51) Int. Cl.
*C07F 1/02* (2006.01)
*C08F 236/10* (2006.01)

(52) U.S. Cl.
CPC .............. *C08F 236/10* (2013.01); *C07F 1/02* (2013.01); *C08F 2810/00* (2013.01)

(58) Field of Classification Search
CPC .......... C08F 4/48; C08F 4/463; C08F 4/6094; C08F 4/6095; C08F 4/6096; C08F 2/60; C08F 2/44; C08F 236/10; C08F 236/06; C07C 211/21; C07C 211/22; C07D 207/06; C07D 211/14; C07D 223/04; C07D 241/04; C07D 265/30; B01J 2219/00033; B01J 2219/00164; C07F 1/02

See application file for complete search history.

(56) References Cited

U.S. PATENT DOCUMENTS

| | | | |
|---|---|---|---|
| 4,397,994 A | 8/1983 | Takeuchi et al. | |
| 5,063,190 A * | 11/1991 | Hargis | C08F 36/04 502/157 |
| 5,491,230 A * | 2/1996 | Lawson | C07F 1/02 540/450 |
| 5,717,043 A * | 2/1998 | Nakayama | C08C 19/30 525/331.9 |
| 5,935,893 A * | 8/1999 | Lawson | C08F 36/04 502/157 |
| 2012/0190770 A1 | 7/2012 | Ito et al. | |
| 2014/0114014 A1 | 4/2014 | Tokimune et al. | |
| 2016/0159957 A1 | 6/2016 | Choi et al. | |
| 2018/0208684 A1* | 7/2018 | Choe | C08F 2/04 |

FOREIGN PATENT DOCUMENTS

| | | |
|---|---|---|
| EP | 3351566 A1 | 7/2018 |
| JP | H09110942 A | 4/1997 |
| JP | 3748277 B2 | 2/2006 |
| JP | 2012167258 A | 9/2012 |
| JP | 2013028781 A | 2/2013 |
| KR | 20110120622 A | 11/2011 |
| KR | 20140047612 A | 4/2014 |
| KR | 20160092227 A | 8/2016 |
| WO | 2017047923 A1 | 3/2017 |

OTHER PUBLICATIONS

International Search Report for Application No. PCT/KR2019/007405, dated Sep. 23, 2019, pp. 1-2.
Database WPI Week 201663, Thomson Scientific, London, GB, AN 2016-48850G, XP002801661.
Extended European Search Report including Written Opinion for Application No. EP19822724.1 dated Feb. 1, 2021, 6 pgs.

* cited by examiner

*Primary Examiner* — Robert C Boyle
(74) *Attorney, Agent, or Firm* — Lerner, David, Littenberg, Krumholz & Mentlik, LLP

(57) ABSTRACT

The present invention relates to a modification polymerization initiator and a method for preparing the same, and the modification polymerization initiator includes a derived unit from a compound represented by Formula 1 and may include various functional groups in a molecule, and thus, may initiate polymerization reaction and introduce a functional group into a polymer chain at the same time.

14 Claims, No Drawings

MODIFICATION POLYMERIZATION INITIATOR AND METHOD FOR PREPARING THE SAME

CROSS-REFERENCE TO RELATED APPLICATIONS

The present application is a national phase entry under 35 U.S.C. § 371 of International Application No. PCT/KR2019/007405 filed Jun. 19, 2019, which claims priority from Korean Patent Application No. 10-2018-0070891 filed Jun. 20, 2018 and Korean Patent Application No. 10-2018-0070890 filed Jun. 20, 2018, all of which are incorporated herein by reference.

TECHNICAL FIELD

The present invention relates to a modification polymerization initiator which is capable of initiating polymerization reaction and introducing a functional group into a polymer chain at the same time, and a method for preparing the same.

Background Art

According to the recent demand for cars having a low fuel consumption ratio, a conjugated diene-based polymer having modulational stability represented by wet skid resistance as well as low rolling resistance, and excellent abrasion resistance and tensile properties is required as a rubber material for tires.

In order to reduce the rolling resistance of tires, there is a method of reducing hysteresis loss of vulcanized rubber, and rebound resilience at 50° C. to 80° C., tan δ, Goodrich heating, or the like is used as an evaluation index of the vulcanized rubber. That is, it is desirable to use a rubber material having high rebound resilience at the above temperature or a low tan δ value or Goodrich heating.

Natural rubbers, polyisoprene rubbers, or polybutadiene rubbers are known as rubber materials having low hysteresis loss, but these rubbers have a limitation of low wet skid resistance. Thus, recently, conjugated diene-based polymers or copolymers such as styrene-butadiene rubbers (hereinafter, referred to as "SBR") and butadiene rubbers (hereinafter, referred to as "BR"), are prepared by emulsion polymerization or solution polymerization to be used as rubbers for tires. Among these polymerization methods, the greatest advantage of the solution polymerization in comparison to the emulsion polymerization is that the vinyl structure content and the styrene content, which specify physical properties of the rubber, may be arbitrarily adjusted and its molecular weight and physical properties may be controlled by coupling or modification. Thus, the SBR prepared by the solution polymerization is widely used as a rubber material for tires because it is easy to change a structure of the finally prepared SBR or BR, and movement of chain terminals may be reduced and a coupling force with a filler such as silica and carbon black may be increased by coupling or modification of the chain terminals.

In case where the solution-polymerized SBR is used as the rubber material for tires, since a glass transition temperature of the rubber is increased by increasing the vinyl content in the SBR, physical properties such as running resistance and braking force, required for tires may be controlled, and fuel consumption may also be reduced by appropriately adjusting the glass transition temperature. The solution-polymerized SBR is prepared by using an anionic polymerization initiator and is being used by coupling or modifying the chain terminals of the polymer thus formed using various modifiers. For example, U.S. Pat. No. 4,397,994 discloses a method of coupling active anions of the chain terminals of a polymer obtained by polymerizing styrene-butadiene using alkyllithium which is a monofunctional initiator in a non-polar solvent, using a binder such as a tin compound.

Meanwhile, solution-polymerized SSBR is prepared using an anionic polymerization initiator, and in this case, the anionic polymerization initiator mostly uses an organolithium compound. The organolithium compound may be used as it is or after modifying to a functional group-containing compound which is capable of imparting a polymer chain with the functional group. For example, there is a method of preparing and using a modification polymerization initiator having a styrene-based structure unit, a conjugated diene-based structure unit or an arylamine structure unit by reacting a styrene-based compound, a conjugated diene-based compound or an arylamine compound with an organolithium compound, but this method is not economically feasible and has limitation in industrial use. Particularly, the obtaining of a modification polymerization initiator using the conjugated diene-based compound is difficult, because the coupling of a functional group with a conjugated diene-based unit is not easy.

For example, JP3748277 discloses an anionic polymerization initiator prepared by reacting an additive in which nitrogen of a cyclic secondary amine is bonded with conjugated diene carbon, with an organolithium compound. However, in case of preparing by the reaction, the cyclic secondary amine remains to act as a scavenger in the reaction, thereby degrading the yield of the anionic polymerization initiator, and accordingly, filtering and purifying processes are definitely required after the reaction.

In another example, a hexamethylene lithium initiator prepared by the reaction of hexamethyleneimine (MHI) and n-butyllithium (BuLi) as shown in the following Reaction 1 is widely known as a modification polymerization initiator used for preparing SSBR:

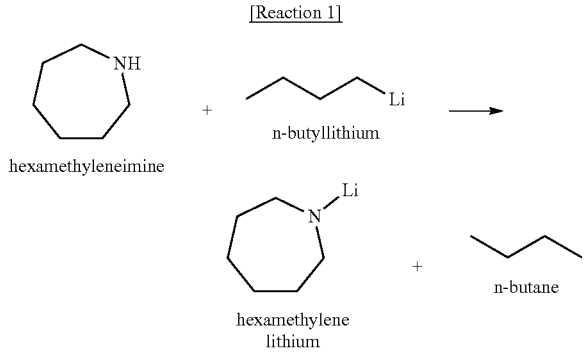

[Reaction 1]

However, the hexamethylene lithium initiator has low solubility with respect to a solvent and is precipitated over time and has a limitation in that reactivity with respect to n-butyllithium is not good though used as a polymerization initiator. In addition, in order to compensate the limitation of the hexamethylene lithium initiator, a method for preparing a modification polymerization initiator by further reacting the hexamethylene lithium synthesized in Reaction 1 with a conjugated diene compound such as isoprene and 1,3-butadiene as in the following Reaction 2 has been suggested:

[Reaction 2]

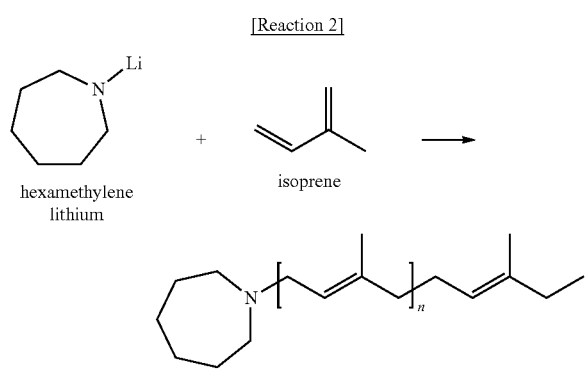

hexamethylene lithium + isoprene →

However, though the modification polymerization initiator thus prepared has improved solubility and reactivity when compared with the hexamethylene lithium initiator, precipitation still takes place over time and deactivation arises.

Meanwhile, an anionic polymerization initiator such as the above-described modification polymerization initiator is generally prepared through a batch type process, or an anionic polymerization initiator and SSBR are simultaneously prepared in one batch type reactor. In the former, the anionic polymerization initiator thus prepared necessarily requires a storage step prior to use for preparing SSBR, and reacts with various scavengers such as humidity and air during storage time to lose activity. As a result, the initiator has adverse effects on a subsequent process and may become a factor degrading the physical properties of the SSBR finally prepared. In the latter, the preparation reaction of an anionic polymerization initiator and SSBR polymerization reaction are performed in the same batch type reactor, and the defects relating to the storage may be solved but it is difficult to confirm if the anionic polymerization initiator is properly synthesized and the physical properties of the SSBR finally prepared are inferior to a case of adding a pre-synthesized anionic polymerization initiator. Further, in the conventional batch type process, by-products may be produced by the direct injection, mixing and reaction of raw materials, or unreacted materials may be produced by reverse reaction, and as a result, there are problems of decreasing yield.

Accordingly, recently, in order to solve the problems of the batch type reactor, a method of using a continuous type reactor is being studied.

For example, Korean Laid-open Patent Publication No. 10-2016-0092227 discloses a method for preparing an anionic polymerization initiator using a continuous type reactor including a static mixer. In case of the method, since concentration distribution of raw materials or temperature distribution may become uniform, lithiation reaction is continuously carried out, and problems relating to storage and problems of decreasing yield may be reduced, but with the use of the static mixer, the problem of the exothermic reaction of the lithiation reaction is not solved, and a special cooling apparatus is required to increase preparation cost.

Accordingly, the development of a modification polymerization initiator having excellent economic feasibility and industrial applicability is required.

DISCLOSURE OF THE INVENTION

Technical Problem

The present invention is devised to solve the above-mentioned problems of the conventional technique, and an object is to provide a modification polymerization initiator which is used in polymerization reaction to easily initiate reaction and provide a polymer with a functional group.

In addition, another object of the present invention is to provide a method for preparing a modification polymerization initiator in a high conversion ratio by minimizing side reactions.

Technical Solution

To solve the above-described tasks, the present invention provides a modification polymerization initiator including at least one derived unit from a compound represented by the following Formula 1 and a derived unit from a compound represented by the following Formula 2:

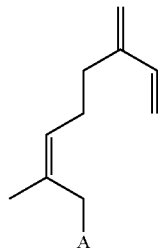

[Formula 1]

in Formula 1,

A is $-NR_aR_b$, $-OR_c$, or $-SR_d$, and $R_a$ to $R_d$ are each independently an alkyl group of 1 to 30 carbon atoms, an alkenyl group of 2 to 30 carbon atoms, an alkynyl group of 2 to 30 carbon atoms, a cycloalkyl group of 3 to 30 carbon atoms, an aryl group of 6 to 30 carbon atoms, a heteroalkyl group of 1 to 30 carbon atoms, a heteroalkenyl group of 2 to 30 carbon atoms, a heteroalkynyl group of 2 to 30 carbon atoms, a heterocycloalkyl group of 2 to 30 carbon atoms or a heteroaryl group of 3 to 30 carbon atoms, where each of $R_a$ to $R_d$ is unsubstituted or substituted with a substituent including one or more heteroatoms selected among N, O, S, Si and F atoms, and $R_a$ and $R_b$ may be combined with each other to form a heterocycle of 3 to 20 carbon atoms with N, which is unsubstituted or substituted with an alkyl group of 1 to 30 carbon atoms, $M-R_e$ [Formula 2]

in Formula 2,

M is an alkali metal, and $R_e$ is hydrogen, an alkyl group of 1 to 30 carbon atoms, an alkenyl group of 2 to 30 carbon atoms, an alkynyl group of 2 to 30 carbon atoms, a cycloalkyl group of 5 to 30 carbon atoms, or an aryl group of 6 to 30 carbon atoms.

In addition, the present invention provides a method for preparing the modification polymerization initiator described above, including a step of reacting a compound represented by the following Formula 1 and a compound represented by the following Formula 2:

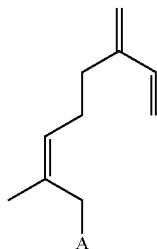

[Formula 1]

in Formula 1,

A is —NR$_a$R$_b$, —OR$_c$, or —SR$_d$, and

R$_a$ to R$_d$ may be each independently an alkyl group of 1 to 30 carbon atoms, an alkenyl group of 2 to 30 carbon atoms, an alkynyl group of 2 to 30 carbon atoms, a cycloalkyl group of 3 to 30 carbon atoms, an aryl group of 6 to 30 carbon atoms, a heteroalkyl group of 1 to 30 carbon atoms, a heteroalkenyl group of 2 to 30 carbon atoms, a heteroalkynyl group of 2 to 30 carbon atoms, a heterocycloalkyl group of 2 to 30 carbon atoms or a heteroaryl group of 3 to 30 carbon atoms, where each of R$_a$ to R$_d$ is unsubstituted or substituted with a substituent including one or more heteroatoms selected among N, O, S, Si and F atoms, and R$_a$ and R$_b$ may be combined with each other to form a heterocycle of 3 to 20 carbon atoms with N, which is unsubstituted or substituted with an alkyl group of 1 to 30 carbon atoms, M-R$_e$     [Formula 2]

in Formula 2,

M is an alkali metal, and

R$_e$ is hydrogen, an alkyl group of 1 to 30 carbon atoms, an alkenyl group of 2 to 30 carbon atoms, an alkynyl group of 2 to 30 carbon atoms, a cycloalkyl group of 5 to 30 carbon atoms, or an aryl group of 6 to 30 carbon atoms.

Advantageous Effects

The modification polymerization initiator according to the present invention may include various functional groups in a molecule by including a derived unit from a compound represented by Formula 1, and thus, may initiate polymerization reaction and introducing a functional group into a polymer chain at the same time.

In addition, according to the method for preparing a modification polymerization initiator according to the present invention, a modification polymerization initiator may be easily prepared, and particularly, the production of an unreacted material during lithiation reaction may be decreased by performing through continuous type reaction using a continuous type reactor, problems due to the exothermic reaction of the lithiation reaction and the generation of by-products may be reduced by rapid removal of heat, and thus, a conversion ratio may be increased and a modification polymerization initiator with high purity may be prepared in high yield.

BEST MODE FOR CARRYING OUT THE INVENTION

Hereinafter, the present invention will be described in more detail in order to assist the understanding of the present invention.

It will be understood that words or terms used in the description and claims of the present invention shall not be interpreted as the meaning defined in commonly used dictionaries. It will be further understood that the words or terms should be interpreted as having a meaning that is consistent with their meaning of the technical idea of the invention, based on the principle that an inventor may properly define the meaning of the words or terms to best explain the invention.

The term "substituted" used in the present invention may mean that hydrogen of a functional group, atomic group or compound is substituted with a specific substituent, and in case where the hydrogen of the functional group, atomic group or compound is substituted with the specific substituent, one or a plurality of two or more substituents may be present according to the number of hydrogen present in the functional group, atomic group or compound. If a plurality of substituents is present, each substituent may be the same or different.

The term "alkyl group" used in the present invention may mean monovalent aliphatic saturated hydrocarbon, and may include both a linear alkyl group such as methyl, ethyl, propyl and butyl, and a branched alkyl group such as isopropyl, sec-butyl, tert-butyl and neo-pentyl.

The term "alkylene group" used in the present invention may mean divalent aliphatic saturated hydrocarbon such as methylene, ethylene, propylene and butylene.

The term "alkenyl group" used in the present invention may mean an alkyl group including one or two or more double bonds.

The term "alkynyl group" used in the present invention may mean an alkyl group including one or two or more triple bonds.

The term "cycloalkyl group" used in the present invention may mean cyclic saturated hydrocarbon.

The term "aryl group" used in the present invention may mean cyclic aromatic hydrocarbon, and may include both monocyclic aromatic hydrocarbon including one ring, and polycyclic aromatic hydrocarbon including two or more bonded rings.

The term "heterocycle" used in the present invention may mean an aliphatic hetero hydrocarbon ring or an aromatic hetero hydrocarbon ring, in which one or more among carbon atoms constituting an aliphatic hydrocarbon ring or an aromatic hydrocarbon ring are substituted with heteroatoms.

The term "derived unit" and "derived functional group" used in the present invention may represent a component or a structure comes from a certain material, or the material itself.

The present invention provides a modification polymerization initiator which acts as a polymerization initiator for initiating polymerization during polymerizing a polymer, particularly, a conjugated diene-based polymer, and at the same time, acts as a modifier introducing a functional group into a polymer chain.

The modification polymerization initiator according to an embodiment of the present invention is characterized in including a derived unit from a compound represented by the following Formula 1 and a derived unit from a compound represented by the following Formula 2:

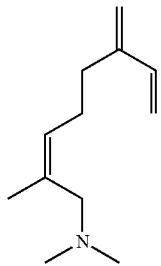

[Formula 1]

in Formula 1,

A is —NR$_a$R$_b$, —OR$_c$, or —SR$_d$, and

R$_a$ to R$_d$ may be each independently an alkyl group of 1 to 30 carbon atoms, an alkenyl group of 2 to 30 carbon atoms, an alkynyl group of 2 to 30 carbon atoms, a cycloalkyl group of 3 to 30 carbon atoms, an aryl group of 6 to 30 carbon atoms, a heteroalkyl group of 1 to 30 carbon atoms, a heteroalkenyl group of 2 to 30 carbon atoms, a heteroalkynyl group of 2 to 30 carbon atoms, a heterocycloalkyl group of 2 to 30 carbon atoms or a heteroaryl group of 3 to 30 carbon atoms, where each of R$_a$ to R$_d$ is unsubstituted or substituted with a substituent including one or more heteroatoms selected among N, O, S, Si and F atoms, and R$_a$ and R$_b$ may be combined with each other to form a heterocycle of 3 to 20 carbon atoms with N, which is unsubstituted or substituted with an alkyl group of 1 to 30 carbon atoms, $$M\text{-}R_e \quad \text{[Formula 2]}$$

in Formula 2,

M is an alkali metal, and

R$_e$ is hydrogen, an alkyl group of 1 to 30 carbon atoms, an alkenyl group of 2 to 30 carbon atoms, an alkynyl group of 2 to 30 carbon atoms, a cycloalkyl group of 5 to 30 carbon atoms, or an aryl group of 6 to 30 carbon atoms.

Particularly, in Formula 1, A is —NR$_a$R$_b$, —OR$_c$, or —SR$_d$, where R$_a$ to R$_d$ may be each independently an alkyl group of 1 to 20 carbon atoms, an alkenyl group of 2 to 20 carbon atoms, an alkynyl group of 2 to 20 carbon atoms, a cycloalkyl group of 3 to 20 carbon atoms, an aryl group of 6 to 20 carbon atoms, a heteroalkyl group of 1 to 20 carbon atoms, a heteroalkenyl group of 2 to 20 carbon atoms, a heteroalkynyl group of 2 to 20 carbon atoms, a heterocycloalkyl group of 2 to 20 carbon atoms or a heteroaryl group of 3 to 20 carbon atoms, where each of R$_a$ to R$_d$ may be unsubstituted or substituted with a substituent including one or more heteroatoms selected among N, O, S, Si and F atoms.

In addition, R$_a$ and R$_b$ in —NR$_a$R$_b$ may be combined with each other to form a heterocycle of 3 to 10 carbon atoms, which is unsubstituted or substituted with an alkyl group of 1 to 10 carbon atoms, where the heterocycle may include one or more heteroatoms selected among 0, S, Si and F atoms in addition to N.

More particularly, in Formula 1, A may be selected from substituents represented by the following Formula 1a to Formula 1c:

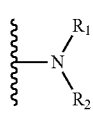

[Formula 1a]

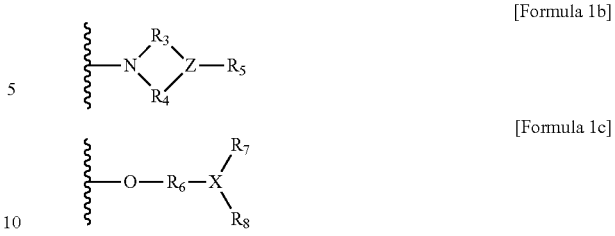

in Formula 1a to Formula 1c,

R$_1$, R$_2$, R$_5$, R$_7$ and R$_8$ may be each independently an alkyl group of 1 to 10 carbon atoms, an alkenyl group of 2 to 10 carbon atoms, an alkynyl group of 2 to 10 carbon atoms, a cycloalkyl group of 3 to 10 carbon atoms, an aryl group of 6 to 10 carbon atoms, a heteroalkyl group of 1 to 10 carbon atoms, a heteroalkenyl group of 2 to 10 carbon atoms, a heteroalkynyl group of 2 to 10 carbon atoms, a heterocycloalkyl group of 3 to 10 carbon atoms, or a heteroaryl group of 3 to 10 carbon atoms, where R$_1$ and R$_2$ may be combined with each other to form an aliphatic hetero hydrocarbon ring of 5 to 20 carbon atoms or an aromatic hetero hydrocarbon ring of 6 to 20 carbon atoms together with N, and R$_7$ and R$_8$ may be combined with each other to form an aliphatic hetero hydrocarbon ring of 5 to 20 carbon atoms or an aromatic hetero hydrocarbon ring of 6 to 20 carbon atoms together with X, and each of R$_1$, R$_2$, R$_5$, R$_7$ and R$_8$ is unsubstituted or substituted with a substituent including one or more heteroatoms selected among N, O and S atoms, R$_3$, R$_4$ and R$_6$ are each independently an alkylene group of 1 to 10 carbon atoms, which is unsubstituted or substituted with an alkyl group of 1 to 10 carbon atoms, a cycloalkyl group of 5 to 10 carbon atoms, an aryl group of 6 to 10 carbon atoms, a heteroatom selected among N and O atoms or a substituent including the heteroatom, and X and Z are each independently one selected among N, O and S atoms, where if X is O or S, R$_8$ is not present, and if Z is O or S, R$_5$ is not present.

Particularly, in Formula 1a to Formula 1c, R$_1$, R$_2$, R$_5$, R$_7$ and R$_8$ are each independently an alkyl group of 1 to 10 carbon atoms or a heteroalkyl group of 1 to 10 carbon atoms, which is unsubstituted or substituted with a substituent including one or more heteroatoms selected among N, O and S atoms, where R$_1$ and R$_2$ are combined with each other to form an aliphatic hetero hydrocarbon ring of 5 to 10 carbon atoms or an aromatic hetero hydrocarbon ring of 6 to 10 carbon atoms together with N, and R$_7$ and R$_8$ may be combined with each other to form an aliphatic hetero hydrocarbon ring of 5 to 20 carbon atoms or an aromatic hetero hydrocarbon ring of 6 to 20 carbon atoms together with X, R$_3$, R$_4$ and R$_6$ are each independently an alkylene group of 1 to 10 carbon atoms, which is unsubstituted or substituted with an alkyl group of 1 to 6 carbon atoms, R$_5$ is an alkyl group of 1 to 10 carbon atoms, and X and Z are each independently one selected among N, O and S atoms, where if X is O or S, R$_8$ may not be present, and if Z is O or S, R$_5$ may not be present.

More particularly, a myrcene derivative compound represented by Formula 1 may be a compound represented by the following Formula 1-1 to Formula 1-11:

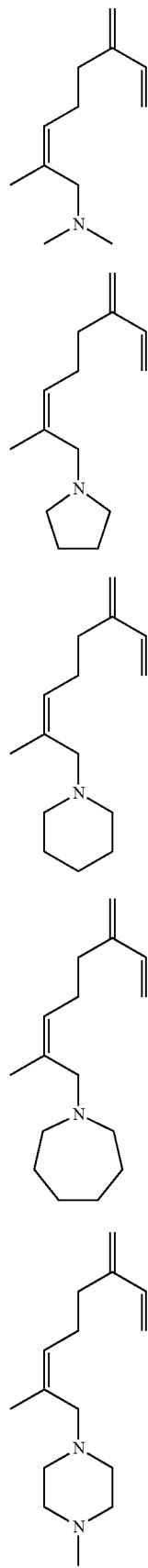
[Formula 1-1]
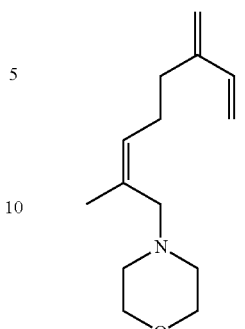
[Formula 1-2]
[Formula 1-3]
[Formula 1-4]
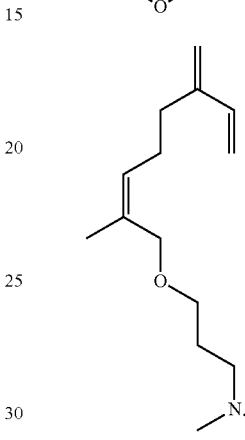
[Formula 1-5]
[Formula 1-6]
[Formula 1-7]
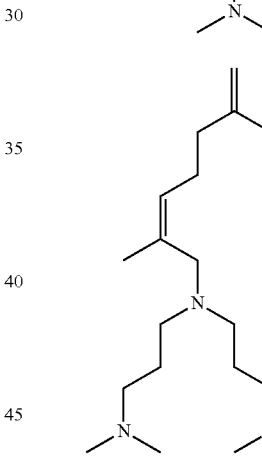
[Formula 1-8]
[Formula 1-9]
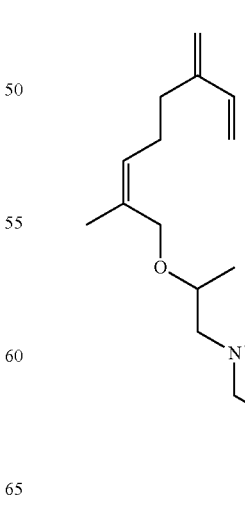

[Formula 1-10]

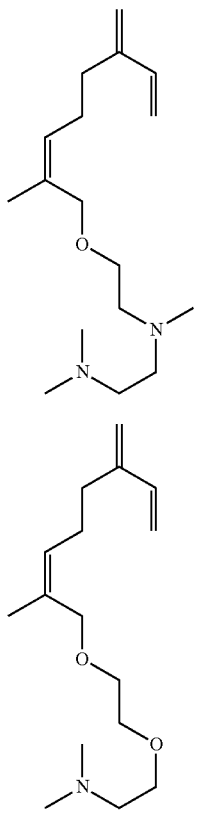

[Formula 1-11]

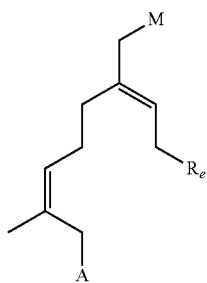

In addition, in Formula 2, M is an alkali metal and $R_e$ may be hydrogen, an alkyl group of 1 to 10 carbon atoms, an alkenyl group of 2 to 10 carbon atoms, an alkynyl group of 2 to 10 carbon atoms, a cycloalkyl group of 5 to 10 carbon atoms or an aryl group of 6 to 10 carbon atoms, particularly, in Formula 2, M may be Na, K or Li and Re may be an alkyl group of 1 to 10 carbon atoms.

In addition, the modification polymerization initiator according to an embodiment of the present invention may be a single material or a mixture type obtained by mixing various materials. Here, the mixture may mean the presence of various isomers together.

Particularly, the modification polymerization initiator may include one or more selected from the group consisting of a compound represented by the following Formula 3 and isomers thereof:

[Formula 3]

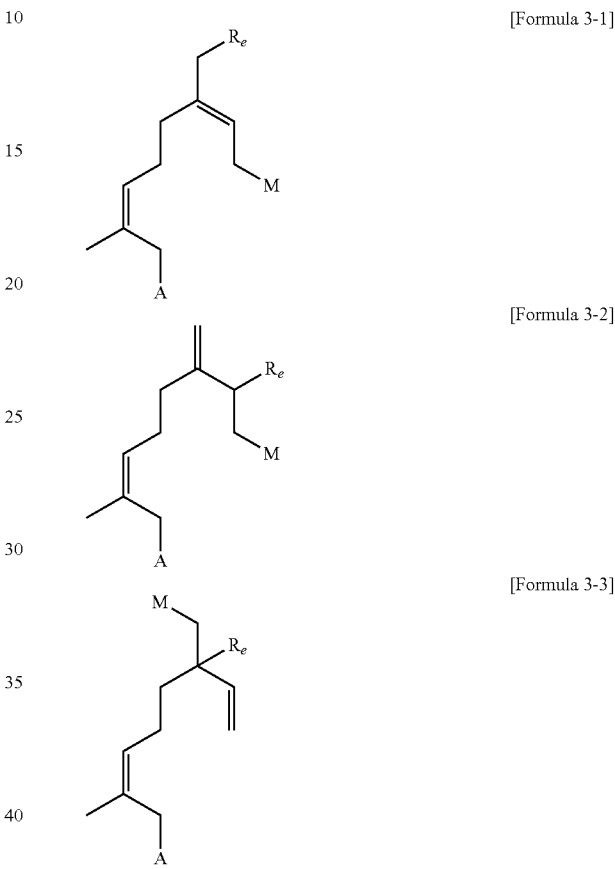

In Formula 3, A is the same as defined in Formula 1, M is Na, K or Li, and $R_e$ is hydrogen or an alkyl group of 1 to 10 carbon atoms. In addition, in Formula 3, M may be bonded to neighboring carbon via an ionic bond.

Meanwhile, the isomer of the compound represented by Formula 3 may include both a structural isomer and a stereoisomer of the compound represented by Formula 3, and for example, a compound represented by the following Formula 3-1 to Formula 3-3:

[Formula 3-1]

[Formula 3-2]

[Formula 3-3]

In Formula 3-1 to Formula 3-3, A, M and $R_e$ are the same as defined in Formula 3.

In addition, the modification polymerization initiator according to an embodiment of the present invention may include one or more selected from a dimer, a trimer and an oligomer of each of the compound represented by Formula 3 and an isomer thereof.

Here, the dimer represents a type in which two derived units from the compound represented by Formula 1 and one derived unit from the compound represented by Formula 2 per molecule, the trimer represents a type in which three derived units from the compound represented by Formula 1 and one derived unit from the compound represented by Formula 2, and the oligomer is a type in which a plurality of derived units from the compound represented by Formula 1 and one derived unit from the compound represented by Formula 2 per molecule.

In addition, the compound represented by Formula 1, according to an embodiment of the present invention may be prepared by reacting myrcene with a functional group compound, for example, prepared through a preparation method including a step of reacting a halogenated myrcene represented by Formula 4 below with an acetylating agent in the presence of a polar organic solvent and a catalyst to prepare an acetylated compound including a compound represented by Formula 5a below and a compound represented by Formula 5b below (step a); a step of hydrolyzing the acetylated compound to prepare a hydroxylated compound (step b); a step of reacting the hydroxylated compound and a leaving group-containing compound to prepare a leaving group-containing compound including a compound represented by Formula 6a below and a compound represented by Formula 6b below (step c); a step of reacting the leaving group-containing compound and a compound represented by Formula 7 below (step d); and a step of purifying (step e).

[Formula 4]

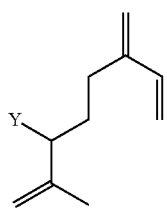

[Formula 5a]

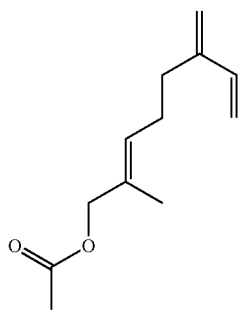

[Formula 5b]

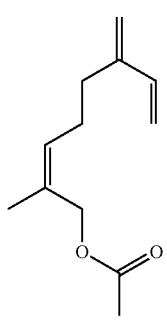

[Formula 6a]

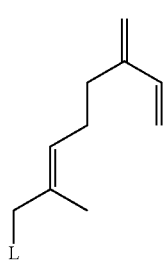

[Formula 6b]

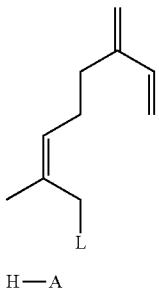

[Formula 7]

H—A

In Formula 4, Formula 5a, Formula 5b, Formula 6a, Formula 6b and Formula 7, A is the same as defined above, L is a leaving group, and Y is Cl, Br or I.

Step a may be performed by reacting a halogenated myrcene represented by Formula 4 and an acetylating agent in the presence of a polar organic solvent and a catalyst, and in this case, the halogenated myrcene, catalyst and acetylating agent may be reacted in a molar ratio of 1:0.1 to 5:1 to 20, at a temperature of 30° C. to 100° C. for 10 minutes to 24 hours.

Here, the acetylating compound is an isomer mixture including a compound represented by Formula 5a and a compound represented by Formula 5b, which are E/Z (cis/trans) isomers, and through the reaction of Step a, the compound represented by Formula 5a and the compound represented by Formula 5b may be formed at the same time from the halogenated myrcene compound represented by Formula 4.

In addition, the polar organic solvent may be a polar aprotic organic solvent or a polar protic organic solvent. The polar aprotic organic solvent may be, for example, one or more selected from the group consisting of N,N-dimethylformamide and dimethyl sulfoxide (DMSO), and the polar protic organic solvent may be one or more selected from the group consisting of acetic acid, n-butanol and n-propanol.

In addition, the catalyst may be one or more selected from the group consisting of sodium iodide (NaI) and sodium bromide (NaBr).

In addition, the acetylating agent may be one or more selected from the group consisting of sodium acetate (NaOAc), acetic acid (HOAc) and acetic anhydride ($Ac_2O$).

In addition, the halogenated myrcene represented by Formula 4 may be prepared by reacting β-myrcene and a halogen-containing compound to introduce a halogen group into the molecular structure of β-myrcene, and in this case, the halogen-containing compound may be a material producing halogenated myrcene through reacting with β-myrcene, for example, calcium hypochlorite ($Ca(OCl)_2$), sodium hypochlorite (NaClO) or hypochlorous acid (HClO).

In addition, the β-myrcene and the halogen-containing compound may be reacted in a molar ratio of 1:0.8 to 1.2, or 1:0.8 to 1.0, without specific limitation, and in this case, the halogenated myrcene represented by Formula 2 may be easily prepared in a high conversion ratio.

In this case, the reaction between the β-myrcene and the halogen-containing compound may be performed in the presence of a reducing agent, and here, the reducing agent plays the role of performing halogenation reaction more easily and may be, for example, carbon dioxide.

Step b is a step for preparing a hydroxylated compound from the acetylated compound and may be performed by hydrolyzing the acetylating compound. In this case, the hydrolysis may be performed by preparing an aqueous solution of an acetylating compound and adding a hydrolysis catalyst.

The aqueous solution of an acetylating compound may include an acetylating compound, an alcohol and water. In this case, the acetylating compound, the alcohol and water in the aqueous solution may provide appropriate concentration of the aqueous solution, for example, the acetylating compound, the alcohol and water may have a molar ratio of 1:10 to 100:5 to 50.

In addition, the hydrolysis catalyst is for catalyze the hydrolysis of the acetylating compound and is not specifically limited. For example, any one or more among potassium carbonate ($K_2CO_3$), sodium carbonate ($Na_2CO_3$) and lithium carbonate ($Li_2CO_3$) may be used. In this case, the hydrolysis catalyst may be used in 0.5 to 10 mol based on 1 mol of the acetylating compound.

Step c is a step for preparing a leaving group-containing compound and may be performed by reacting the hydroxylated compound and a leaving group-containing compound. Particularly, the hydroxylated compound and the leaving group-containing compound may be reacted in a molar ratio of 1:0.5 to 5.

In the above, the leaving group-containing compound is a material reacting with the hydroxylated compound and providing a leaving group corresponding to L in compounds represented by Formula 6a and Formula 6b, for example an alkylsulfonate group such as methanesulfonate group ($CH_3SO_3^-$) and methylbenzenesulfonate group ($C_7H_7SO_3^-$), and any material may be used without specific limitation as long as it may react with the hydroxylated compound and provide the leaving group. For example, methanesulfonyl chloride, p-toluenesulfonyl chloride, 2-propanesulfonyl chloride, trichloromethanesulfonyl chloride, cyclohexanesulfonyl chloride or cyclopentanesulfonyl chloride, may be used.

Step d is a step for preparing an isomer composition including a compound represented by Formula 1 which introduces a functional group derived from a compound represented by Formula 7, and may be performed by reacting the leaving group-containing compound and the compound represented by Formula 7. In this case, the leaving group-containing compound and the compound represented by Formula 7 may be reacted in a molar ratio of 1:0.1 to 20, or 1:0.1 to 10.

Step e is a step for separating and obtaining the compound represented by Formula 1 from the isomer composition through purifying, and may be performed through a common method in the art.

In addition, the present invention provides a method for preparing the modification polymerization initiator.

The method for preparing the modification polymerization initiator according to an embodiment of the present invention is characterized in including a step of reacting a compound represented by the following Formula 1 and a compound represented by the following Formula 2:

[Formula 1]

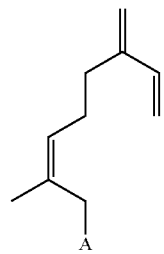

In Formula 1 and Formula 2, A, M and $R_e$ are the same as defined above.

The compound represented by Formula 1 and the compound represented by Formula 2 may be reacted in a molar ratio of 1:0.5 to 5 and may be performed in a temperature range of 0° C. to 80° C. under pressure conditions of 0.5 bar to 10 bar.

Particularly, the preparation method according to an embodiment of the present invention may be performed by batch type reaction or continuous type reaction. In case of the batch type reaction, the compound represented by Formula 1 and the compound represented by Formula 2 may be reacted in a molar ratio of 1:0.5 to 3, more particularly, the compound represented by Formula 1 and the compound represented by Formula 2 may be reacted in a molar ratio of 1:1 to 2.

In addition, the reaction of the compound represented by Formula 1 and the compound represented by Formula 2 may be performed in a temperature range of 0° C. to 45° C. and under an atmospheric pressure or more, particularly, in a temperature range of 20° C. to 30° C. and under pressure conditions of 0.5 bar to 2 bar.

In another embodiment, in the preparation method according to an embodiment of the present invention, the reaction of the compound represented by Formula 1 and the compound represented by Formula 2 may be performed in a continuous type reactor, and in this case, the continuous type reactor may mean a reactor performing reaction while continuously injecting raw materials used in the reaction.

Particularly, the reaction may be performed in the continuous type reactor including a first channel and a second channel, and prior to performing the reaction, the first reactant including the compound represented by Formula 1 may be injected through the first channel to the continuous type reactor and the second reactant including the compound represented by Formula 2 may be injected through the second channel to the continuous type reactor.

Here, the first channel and the second channel may mean injection parts (or inputting parts) for controlling the injection amounts of the first reactant and the second reactant, respectively, in the continuous type reactor, and in this case, the injection amounts of the first reactant and the second reactant may be each independently controlled. Through this, each injection amount may be controlled according to reaction environments and side reactions may be minimized.

In addition, the first reactant may be injected through the first channel in a rate of 1.0 g/min to 20.0 g/min to the continuous type reactor, and the second reactant may be injected through the second channel in a rate of 1.0 g/min to 20.0 g/min to the continuous type reactor. Particularly, the first reactant may be injected through the first channel in a rate of 1.0 g/min to 10.0 g/min to the continuous type reactor, and the second reactant may be injected through the second channel in a rate of 1.0 g/min to 10.0 g/min to the continuous type reactor. Within these ranges, the injection amounts of the compound represented by Formula 1 and the compound represented by Formula 2 may be appropriately controlled without rapid change, thereby minimizing side reactions.

In addition, during the reaction, the compound represented by Formula 1 and the compound represented by Formula 2 may be reacted in a molar ratio of 1:0.5 to 1:5, and particularly, the compound represented by Formula 1 and the compound represented by Formula 2 may be reacted in a molar ratio of 1:0.8 to 1:1.5. If the compound represented by Formula 1 and the compound represented by Formula 2 are reacted in the above-described molar ratio, side reactions may be decreased.

In addition, in the preparation method according to an embodiment of the present invention, by controlling the injection rate (flowing amount) and molar ratio of the first reactant and the second reactant as described above, a modification polymerization initiator in a polymer type of a monomer or a dimer may be prepared.

Meanwhile, the first reactant may be a material having flowability so that the compound represented by Formula 1 may be easily injected to the continuous type reactor to participate in the reaction, for example, the first reactant may be the compound represented by Formula 1 itself, or a solution including the compound represented by Formula 1 and a reaction solvent.

In addition, the second reactant may be a material having flowability so that the compound represented by Formula 2 may be easily injected to the continuous type reactor to participate in the reaction, for example, the second reactant may be the compound represented by Formula 2 itself, or a solution including the compound represented by Formula 2 and a reaction solvent.

Here, in case where the first reactant and the second reactant are solutions, the concentration of the solution is not specifically limited and may be controlled so that the compound represented by Formula 1 and the compound represented by Formula 2 may have the above-described molar ratio.

In addition, the reaction solvent may be a hydrocarbon solvent which does not react with anions, for example, one or more selected among a linear hydrocarbon compound such as pentane, hexane and octane; a branched derivative thereof; a cyclic hydrocarbon compound such as cyclohexane and cycloheptane; an aromatic hydrocarbon compound such as benzene, toluene and xylene; and liner or cyclic ethers such as dimethyl ether, diethyl ether, anisole and tetrahydrofuran. Particularly, the reaction solvent may be cyclohexane, hexane, tetrahydrofuran or diethyl ether.

In addition, the reaction may be performed in the presence of a polar additive to control the reactivity of the compound represented by Formula 1 and the compound represented by Formula 2. In this case, the polar additive is not specifically limited but may include, for example, one or more selected from the group consisting of tetrahydrofuran, ditetrahydrofurylpropane, diethyl ether, cycloamyl ether, dipropyl ether, ethylene dimethyl ether, ethylene diethyl ether, diethyl glycol, dimethyl glycol, tert-butoxyethoxyethane, bis(3-dimethylamino ethyl) ether, (dimethylamino ethyl) ethyl ether, trimethylamine, triethylamine, tripropylamine and tetramethylethylenediamine.

Meanwhile, in case of performing the reaction in a continuous type reactor, the polar additive may be injected into the continuous type reactor by being contained in the first reactant or the second reactant, and particularly, the polar additive may be injected into the continuous type reactor by being contained in the first reactant.

That is, the first reactant may include a polar additive, and in this case, the polar additive may be included in the first reactant in a molar ratio of 1.0 to 5.0 with respect to 1 mol of the compound represented by Formula 1. Within this range, the reactivity between the compound represented by Formula 1 and the compound represented by Formula 2 may be appropriately controlled to easily carry out the reaction and decrease side reactions.

Meanwhile, in the preparation method of the modification polymerization initiator according to the present invention, in case of performing the reaction by the continuous type reaction in the continuous type reactor, the mixing ratio of reaction raw materials (for example, the compound represented by Formula 1 and the compound represented by Formula 2) during lithiation reaction may be increased to decrease the production of unreacted material, and the production of by-products may be decreased by reducing problems due to the exothermic reaction of the lithiation reaction by rapid removal of heat. As a result, a conversion ratio may be improved and a modification polymerization initiator with high purity may be stably prepared in high yield.

Also, the present invention provides a modified conjugated diene-based polymer including a functional group derived from the modification polymerization initiator.

The modified conjugated diene-based polymer according to an embodiment of the present invention includes a repeating unit derived from a conjugated diene-based monomer and may include a functional group derived from the modification polymerization initiator in at least one terminal.

Here, the repeating unit derived from the conjugated diene-based monomer may mean a repeating unit formed during polymerizing a conjugated diene-based monomer, and the conjugated diene-based monomer may be one or more selected from the group consisting of 1,3-butadiene, 2,3-dimethyl-1,3-butadiene, piperylene, 3-butyl-1,3-octadiene, isoprene, 2-phenyl-1,3-butadiene, and 2-halo-1,3-butadiene (halo means a halogen atom).

Meanwhile, the modified conjugated diene-based polymer may be, for example, a copolymer further including a repeating unit derived from an aromatic vinyl-based monomer together with the repeating unit derived from the conjugated diene-based monomer, and the repeating unit derived from the aromatic vinyl-based monomer may mean a repeating unit formed by an aromatic vinyl-based monomer during polymerizing. Here, the aromatic vinyl-based monomer may be, for example, one or more selected from the group consisting of styrene, α-methylstyrene, 3-methylstyrene, 4-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene.

Hereinafter, the present invention will be explained in more detail referring to embodiments. However, the embodiments are provided for illustrating the present invention, and the scope of the present invention is not limited thereto.

Example 1

A reactor in an inert state was prepared through purging with nitrogen for a constant time and applying vacuum.

The internal temperature of the reactor was controlled to 25° C. and the internal pressure was controlled to 1 bar, and then, 16.1 g of n-hexane, 0.7 g (6.2 mmol) of tetramethylethyleneamine, 1.7 g (6.2 mmol in hexane) of 2.5 M n-butyllithium, and 6.2 mmol of a compound represented by Formula 1-5 below were injected in order into the reactor, followed by stirring for 1 minute to prepare a modification polymerization initiator including a compound represented by Formula i below and a compound represented by Formula v below. The synthesis of the modification polymerization initiator thus prepared was confirmed by the change of molecular weights between the compound represented by Formula 1-5 and a finally obtained material through GC/MS analysis. From MS analysis results, m/z=292 g/mol and 526 g/mol, and the molecular weight of the compound represented by Formula 1-5 as a starting material was 234 g/mol. In this case, the GC/MS analysis results of the modification polymerization initiator represented that Li in the modification polymerization initiator was substituted with H.

Particularly, for the GC/MS analysis, ZB-5MS (0.25 mm (ID)×30 ml, 0.25 μm d.f. capillary) was used as a column, a gas flow rate (column (He)) was 1 ml/min, the oven temperature was initially 50° C., elevated to 320° C. after 3 minutes in a rate of 10° C./min and kept for 15 minutes, the injector temperature was 250° C., a split ratio was 1/20, and an injection amount was controlled to 0.2 μl. In addition, the modification polymerization initiator was measured after quenching for the protonation of an organolithium part.

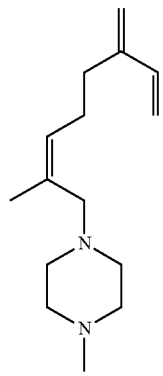

[Formula 1-5]

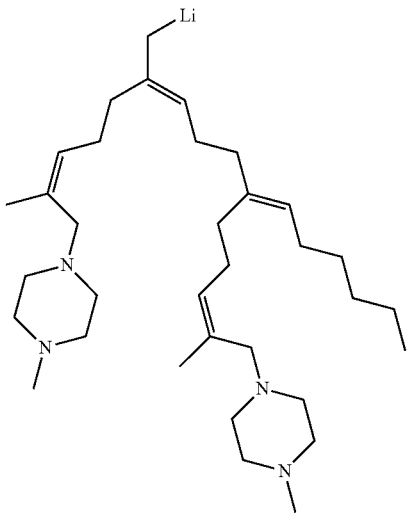

[Formula v]

Example 2

A reactor in an inert state was prepared through purging with nitrogen for a constant time and applying vacuum.

The internal temperature of the reactor was controlled to 25° C. and the internal pressure was controlled to 1 bar, and then, 16.1 g of n-hexane, 0.7 g (6.2 mmol) of tetramethylethyleneamine, 1.7 g (6.2 mmol in n-hexane) of 2.5 M n-butyllithium, and 6.2 mmol of a compound represented by Formula 1-7 below were injected in order into the reactor, followed by stirring for 1 minute to prepare a modification polymerization initiator including a compound represented by Formula ii below and a compound represented by Formula vi below. The synthesis of the modification polymerization initiator thus prepared was confirmed by the change of molecular weights between the compound represented by Formula 1-7 and a finally obtained material through GC/MS analysis. From MS analysis results, m/z=295 g/mol and 539 g/mol, and the molecular weight of the compound represented by Formula 1-7 as a starting material was 237 g/mol. In this case, the GC/MS analysis results of the modification polymerization initiator represented that Li in the modification polymerization initiator was substituted with H. GC/MS analysis was performed by the same method as in Example 1.

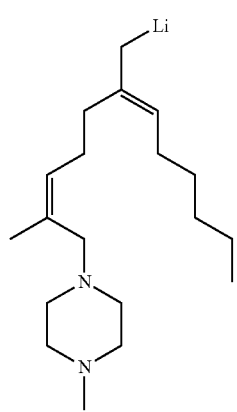

[Formula i]

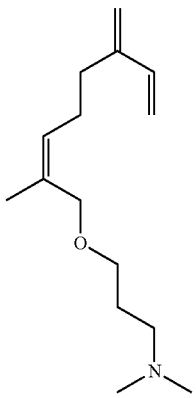

[Formula 1-7]

-continued

[Formula ii]

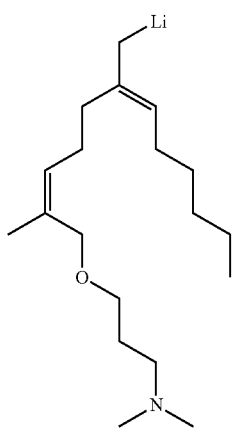

[Formula vi]

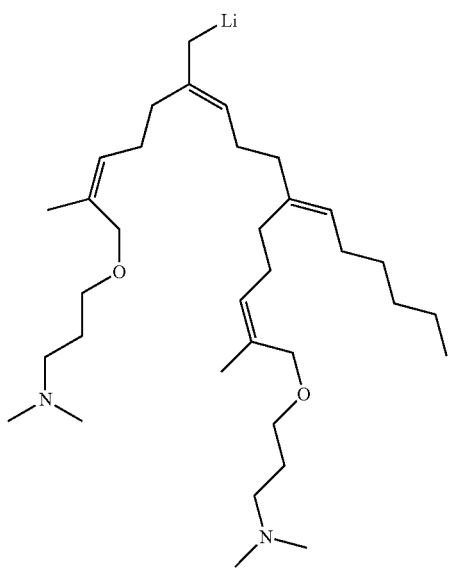

Example 3

A reactor in an inert state was prepared through purging with nitrogen for a constant time and applying vacuum.

The internal temperature of the reactor was controlled to 25° C. and the internal pressure was controlled to 1 bar, and then, 16.1 g of n-hexane, 0.7 g (6.2 mmol) of tetramethylethyleneamine, 1.7 g (6.2 mmol in n-hexane) of 2.5 M n-butyllithium, and 6.2 mmol of a compound represented by Formula 1-6 below were injected in order into the reactor, followed by stirring for 1 minute to prepare a modification polymerization initiator including a compound represented by Formula iii below. The synthesis of the modification polymerization initiator thus prepared was confirmed by the change of molecular weights between the compound represented by Formula 1-6 and a finally obtained material through GC/MS analysis. From MS analysis results, m/z=279 g/mol, and the molecular weight of the compound represented by Formula 1-6 as a starting material was 221 g/mol. In this case, the GC/MS analysis results of the modification polymerization initiator represented that Li in the modification polymerization initiator was substituted with H. GC/MS analysis was performed by the same method as in Example 1.

[Formula 1-6]

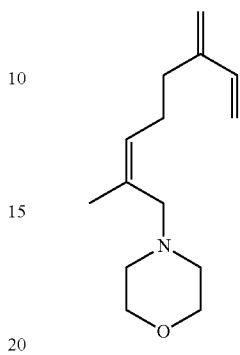

[Formula iii]

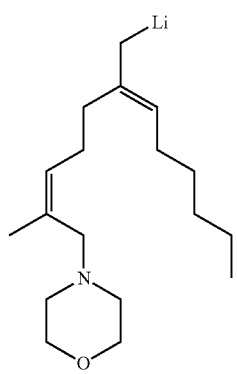

Example 4

A reactor in an inert state was prepared through purging with nitrogen for a constant time and applying vacuum.

The internal temperature of the reactor was controlled to 25° C. and the internal pressure was controlled to 1 bar, and then, 16.1 g of n-hexane, 0.7 g (6.2 mmol) of tetramethylethyleneamine, 1.7 g (6.2 mmol in n-hexane) of 2.5 M n-butyllithium, and 6.2 mmol of a compound represented by Formula 1-1 below were injected in order into the reactor, followed by stirring for 1 minute to prepare a modification polymerization initiator including a compound represented by Formula iv below. The synthesis of the modification polymerization initiator thus prepared was confirmed by the change of molecular weights between the compound represented by Formula 1-1 and a finally obtained material through GC/MS analysis. From MS analysis results, m/z=237 g/mol, and the molecular weight of the compound represented by Formula 1-1 as a starting material was 179 g/mol. In this case, the GC/MS analysis results of the modification polymerization initiator represented that Li in the modification polymerization initiator was substituted with H. GC/MS analysis was performed by the same method as in Example 1.

[Formula 1-1]

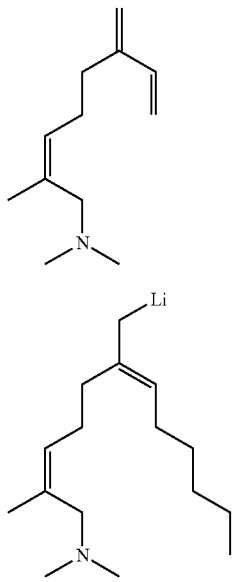

Example 5

A reactor in an inert state was prepared through purging with nitrogen for a constant time and applying vacuum.

The internal temperature of the reactor was controlled to 25° C. and the internal pressure was controlled to 1 bar, and then, 16.1 g of n-hexane, 0.7 g (6.2 mmol) of tetramethylethyleneamine, 1.7 g (6.2 mmol in n-hexane) of 2.5 M n-butyllithium, and 12.4 mmol of a compound represented by Formula 1-5 below were injected in order into the reactor, followed by stirring for 10 minute to prepare a modification polymerization initiator including a compound represented by Formula v below. The synthesis of the modification polymerization initiator thus prepared was confirmed by the change of molecular weights between the compound represented by Formula 1-5 and a finally obtained material through GC/MS analysis. From MS analysis results, m/z=526 g/mol, and the molecular weight of the compound represented by Formula 1-5 as a starting material was 234 g/mol. In this case, the GC/MS analysis results of the modification polymerization initiator represented that Li in the modification polymerization initiator was substituted with H. GC/MS analysis was performed by the same method as in Example 1.

[Formula 1-5]

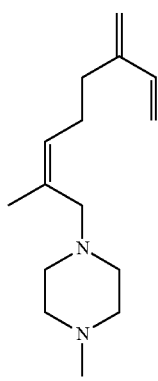

[Formula iv]

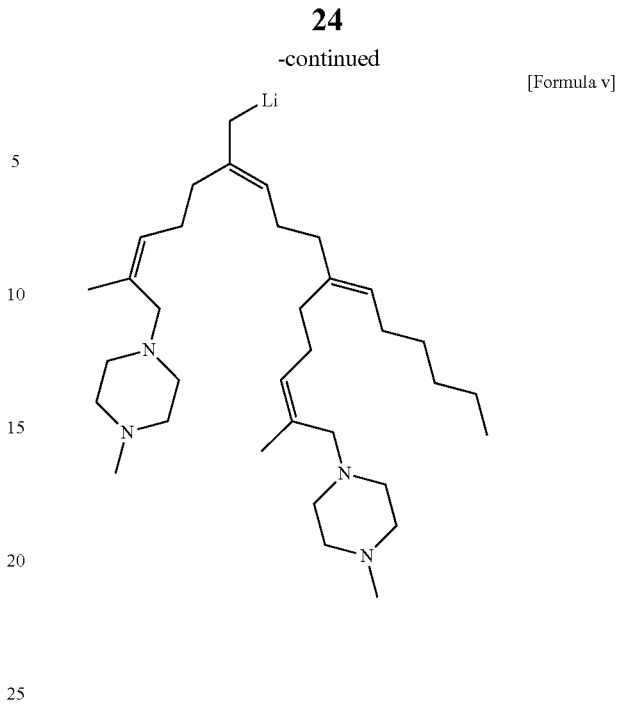

Example 6

Two 2 L, vacuum dried stainless steel pressure vessels were prepared. To the first pressure vessel, 1740 g of hexane, 1.4 mol of a compound represented by Formula 1-5 below, and 1.4 mol of tetramethylethylenediamine were injected to prepare a first reactant. At the same time, to the second pressure vessel, 385 g of 2.5 M n-butyllithium and 1845 g of hexane were injected to prepare a second reactant which was a n-butyllithium solution of 4 wt % (1.4 mol). In a state of maintaining the pressure of each pressure vessel to 5 bar, into a continuous type reactor using a mass flowmeter, the first reactant was injected via a first channel in an injection rate of 1.0 g/min and the second reactant was injected via a second channel in an injection rate of 1.0 g/min, respectively. After that, the reaction was performed for 5 minutes while maintaining the temperature of the continuous type reactor to 25° C. and the internal pressure to bar using a backpressure regulator to prepare a modification polymerization initiator including a compound represented by Formula i below. The synthesis of the modification polymerization initiator thus prepared was confirmed by the change of molecular weights between the compound represented by Formula 1-5 and a finally obtained material through GC/MS analysis. From MS analysis results, m/z=292 g/mol, and the molecular weight of the compound represented by Formula 1-5 as a starting material was 234 g/mol. In this case, the GC/MS analysis results of the modification polymerization initiator represented that Li in the modification polymerization initiator was substituted with H. GC/MS analysis was performed by the same method as in Example 1.

[Formula 1-5]

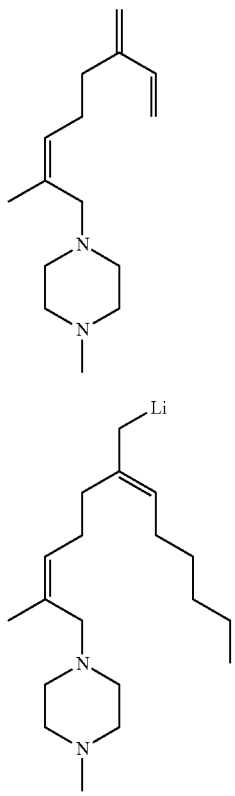

[Formula i]

Example 7

Two 2 L, vacuum dried stainless steel pressure vessels were prepared. To the first pressure vessel, 1740 g of hexane, 1.4 mol of a compound represented by Formula 1-7 below, and 1.4 mol of tetramethylethylenediamine were injected to prepare a first reactant. At the same time, to the second pressure vessel, 385 g of 2.5 M n-butyllithium and 1845 g of hexane were injected to prepare a second reactant which was a n-butyllithium solution of 4 wt % (1.4 mol). In a state of maintaining the pressure of each pressure vessel to bar, into the continuous type reactor using a mass flowmeter, the first reactant was injected via a first channel in an injection rate of 1.0 g/min and the second reactant was injected via a second channel in an injection rate of 1.0 g/min, respectively. After that, the reaction was performed for 5 minutes while maintaining the temperature of the continuous type reactor to 25° C. and the internal pressure to 2 bar using a backpressure regulator to prepare a modification polymerization initiator including a compound represented by Formula ii below. The synthesis of the modification polymerization initiator thus prepared was confirmed by the change of molecular weights between the compound represented by Formula 1-7 and a finally obtained material through GC/MS analysis. From MS analysis results, m/z=295 g/mol, and the molecular weight of the compound represented by Formula 1-7 as a starting material was 237 g/mol. In this case, the GC/MS analysis results of the modification polymerization initiator represented that Li in the modification polymerization initiator was substituted with H. GC/MS analysis was performed by the same method as in Example 1.

[Formula 1-7]

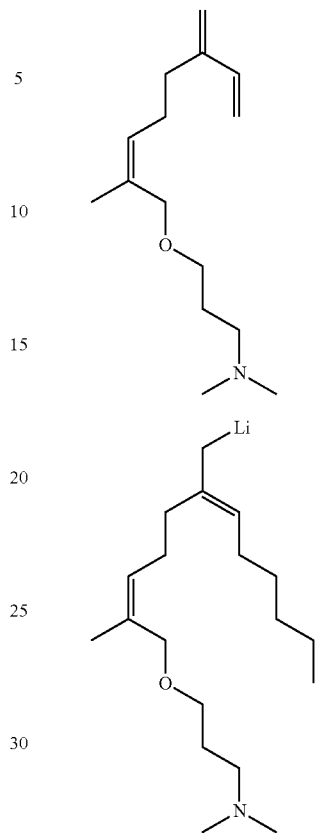

[Formula ii]

Example 8

Two 2 L, vacuum dried stainless steel pressure vessels were prepared. To the first pressure vessel, 1740 g of hexane, 1.4 mol of a compound represented by Formula 1-6 below, and 1.4 mol of tetramethylethylenediamine were injected to prepare a first reactant. At the same time, to the second pressure vessel, 385 g of 2.5 M n-butyllithium and 1845 g of hexane were injected to prepare a second reactant which was a n-butyllithium solution of 4 wt % (1.4 mol). In a state of maintaining the pressure of each pressure vessel to 5 bar, into the continuous type reactor using a mass flowmeter, the first reactant was injected via a first channel in an injection rate of 1.0 g/min and the second reactant was injected via a second channel in an injection rate of 1.0 g/min, respectively. After that, the reaction was performed for 5 minutes while maintaining the temperature of the continuous type reactor to 25° C. and the internal pressure to 2 bar using a backpressure regulator to prepare a modification polymerization initiator including a compound represented by Formula iii below. The synthesis of the modification polymerization initiator thus prepared was confirmed by the change of molecular weights between the compound represented by Formula 1-6 and a finally obtained material through GC/MS analysis. From MS analysis results, m/z=279 g/mol, and the molecular weight of the compound represented by Formula 1-6 as a starting material was 221 g/mol. In this case, the GC/MS analysis results of the modification polymerization initiator represented that Li in the modification polymerization initiator was substituted with H. GC/MS analysis was performed by the same method as in Example 1.

[Formula 1-6]

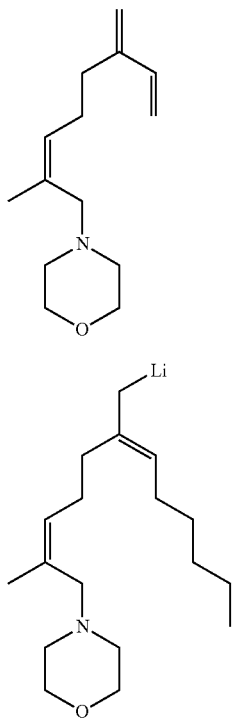

[Formula 1-1]

[Formula iii]

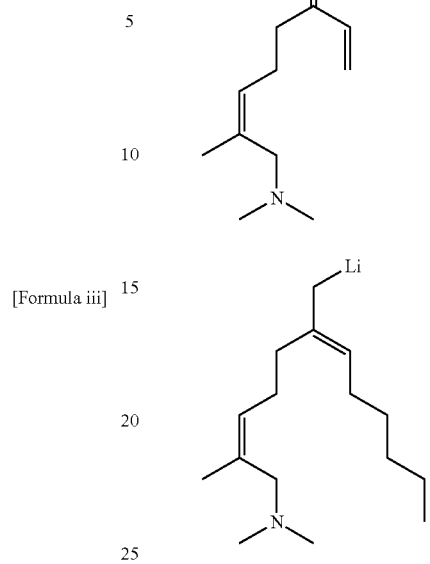

[Formula iv]

Example 9

Two 2 L, vacuum dried stainless steel pressure vessels were prepared. To the first pressure vessel, 1740 g of hexane, 1.4 mol of a compound represented by Formula 1-1 below, and 1.4 mol of tetramethylethylenediamine were injected to prepare a first reactant. At the same time, to the second pressure vessel, 385 g of 2.5 M n-butyllithium and 1845 g of hexane were injected to prepare a second reactant which was a n-butyllithium solution of 4 wt % (1.4 mol). In a state of maintaining the pressure of each pressure vessel to bar, into the continuous type reactor using a mass flowmeter, the first reactant was injected via a first channel in an injection rate of 1.0 g/min and the second reactant was injected via a second channel in an injection rate of 1.0 g/min, respectively. After that, the reaction was performed for 5 minutes while maintaining the temperature of the continuous type reactor to 25° C. and the internal pressure to 2 bar using a backpressure regulator to prepare a modification polymerization initiator including a compound represented by Formula iv below. The synthesis of the modification polymerization initiator thus prepared was confirmed by the change of molecular weights between the compound represented by Formula 1-1 and a finally obtained material through GC/MS analysis. From MS analysis results, m/z=237 g/mol, and the molecular weight of the compound represented by Formula 1-6 as a starting material was 179 g/mol. In this case, the GC/MS analysis results of the modification polymerization initiator represented that Li in the modification polymerization initiator was substituted with H. GC/MS analysis was performed by the same method as in Example 1.

Example 10

In Example 1, a modification polymerization initiator was prepared through the same method as in Example 6 except for injecting a first reactant including a compound represented by Formula 1-5 via a first channel in an injection rate of 20.0 g/min and the second reactant including n-butyllithium via a second channel in an injection rate of 20.0 g/min, respectively, and reacting.

The synthesis of the modification polymerization initiator thus prepared was confirmed by the change of molecular weights between the compound represented by Formula 1-5 and a finally obtained material through GC/MS analysis. From MS analysis results, m/z=292 g/mol, and the molecular weight of the compound represented by Formula 1-5 as a starting material was 234 g/mol. In this case, the GC/MS analysis results of the modification polymerization initiator represented that Li in the modification polymerization initiator was substituted with H. GC/MS analysis was performed by the same method as in Example 1.

[Formula 1-5]

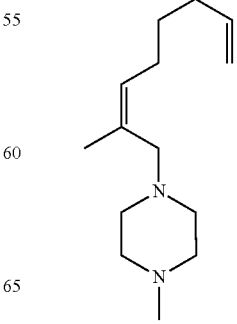

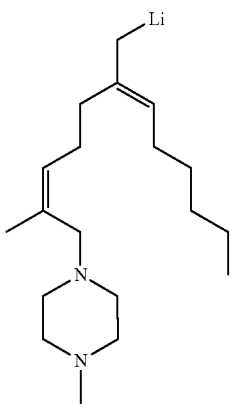

Example 11

In Example 1, a modification polymerization initiator including a compound represented by Formula v below, which had a dimer structure was prepared through the same method as in Example 6 except for injecting a first reactant including a compound represented by Formula 1-5 via a first channel in an injection rate of 10.0 g/min and the second reactant including n-butyllithium via a second channel in an injection rate of 5.0 g/min, respectively, and reacting.

The synthesis of the modification polymerization initiator thus prepared was confirmed by the change of molecular weights between the compound represented by Formula 1-5 and a finally obtained material through GC/MS analysis. From MS analysis results, m/z=526 g/mol, and the molecular weight of the compound represented by Formula 1-5 as a starting material was 234 g/mol. In this case, the GC/MS analysis results of the modification polymerization initiator represented that Li in the modification polymerization initiator was substituted with H. GC/MS analysis was performed by the same method as in Example 1.

[Formula 1-5]

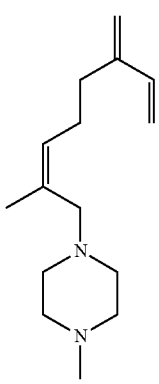

[Formula i]

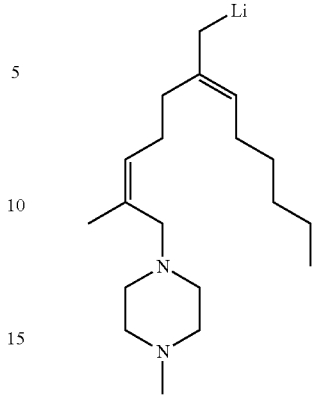

[Formula v]

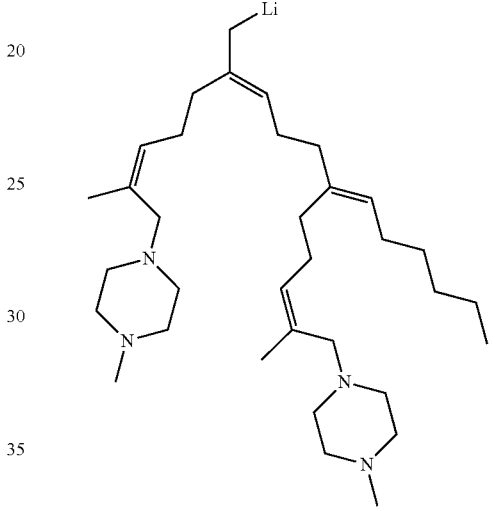

EXPERIMENTAL EXAMPLES

The final conversion ratio (yield) of and a ratio of a monomer and a dimer in a modification polymerization initiator were compared and analyzed for each of the modification polymerization initiators of Example 1, Example 2, and Example 6 to Example 11, and the results are shown in Table 1 below. Here, the conversion ratio was confirmed as the ratio of a material corresponding to Formula 1, which was used for the reaction and a material corresponding to Formula 1 in a final product, based on a material corresponding to Formula 1.

TABLE 1

| Division | Conversion ratio (%) | Monomer ratio (mol %) | Dimer ratio (mol %) |
| --- | --- | --- | --- |
| Example 1 | ≤95 | 70 | 30 |
| Example 2 | ≤90 | 80 | 20 |
| Example 6 | ≥95 | 100 | 0 |
| Example 7 | ≥90 | 100 | 0 |
| Example 8 | 100 | 100 | 0 |
| Example 9 | 100 | 100 | 0 |
| Example 10 | 100 | 100 | 0 |
| Example 11 | ≥90 | 0 | 100 |

As shown in Table 1, Example 1, Example 2, and Example 6 to Example 11 were all confirmed to produce modification polymerization initiators in a high conversion ratio. Particularly, Example 6 to Example 11 were confirmed to produce modification polymerization initiators with high purity in high yield. In addition, it was confirmed that in Example 1 and Example 2, modification polymerization initiators in a mixture type obtained by mixing a monomer and a dimer were prepared, but in Example 6 to Example 11, single materials of a monomer or a dimer were prepared. Through this, it was confirmed that in case of performing through continuous type reaction according to an embodiment of the present invention, a single material of a monomer or a dimer could be selectively prepared by controlling the flowing amount of the reactant injected into a continuous reactor.

Example 12 to Example 22

Modified conjugated diene-based polymers including a functional group derived from the modification polymerization initiator, were prepared using the modification polymerization initiators prepared in Example 1 to Example 11, respectively.

Into a 20 L, autoclave reactor, 21 g of styrene, 58 g of 1,3-butadiene and 581 g of n-hexane were injected in the presence of each of the modification polymerization initiators prepared in Example 1 to Example 11, followed by performing polymerization while elevating the temperature from 50° C. to 80° C. until a polymerization conversion ratio reached 99%. Then, a small amount of 1,3-butadiene was injected for capping the terminal of a polymer with butadiene, and 14 g of a solution in which 30 wt % of Wingstay K antioxidant was dissolved in hexane was added. The polymer thus obtained was put in hot water heated with steam, stirred to remove solvents, and roll-dried to remove a remaining amount of the solvent and water to prepare a modified conjugated diene-based copolymer. Elementary analysis on each copolymer thus prepared was performed to confirm that a nitrogen atom was present in a copolymer chain.

The invention claimed is:

1. A modification polymerization initiator, comprising at least one product derived from a reaction between a compound represented by the following Formula 1 and a compound represented by the following Formula 2:

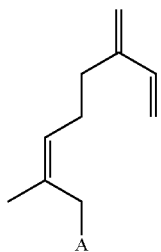

[Formula 1]

in Formula 1,

A is —$NR_aR_b$, —$OR_c$, or —$SR_d$, and $R_a$ to $R_d$ are each independently an alkyl group of 1 to 30 carbon atoms, an alkenyl group of 2 to 30 carbon atoms, an alkynyl group of 2 to 30 carbon atoms, a cycloalkyl group of 3 to 30 carbon atoms, an aryl group of 6 to 30 carbon atoms, a heteroalkyl group of 1 to 30 carbon atoms, a heteroalkenyl group of 2 to 30 carbon atoms, a heteroalkynyl group of 2 to 30 carbon atoms, a heterocycloalkyl group of 2 to 30 carbon atoms or a heteroaryl group of 3 to 30 carbon atoms, where each of $R_a$ to Rd is unsubstituted or substituted with a substituent comprising one or more heteroatoms selected from N, O, S, Si or F atoms, and $R_a$, $R_b$, and N, to which $R_a$ and $R_b$ are attached, are optionally combined with each other to form a heterocycle of 3 to 20 carbon atoms, which is unsubstituted or substituted with an alkyl group of 1 to 30 carbon atoms, M-$R_e$ [Formula 2]

in Formula 2,

M is an alkali metal, and $R_e$ is hydrogen, an alkyl group of 1 to 30 carbon atoms, an alkenyl group of 2 to 30 carbon atoms, an alkynyl group of 2 to 30 carbon atoms, a cycloalkyl group of 5 to 30 carbon atoms, or an aryl group of 6 to 30 carbon atoms.

2. The modification polymerization initiator of claim 1, wherein in Formula 1, A is selected from substituents represented by the following Formula 1a, 1b or 1c:

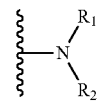

[Formula 1a]

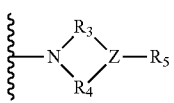

[Formula 1b]

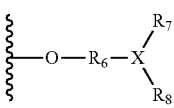

[Formula 1c]

in Formula 1a to Formula 1c, $R_1$, $R_2$, $R_5$, $R_7$ and $R_8$ are each independently an alkyl group of 1 to 10 carbon atoms, an alkenyl group of 2 to 10 carbon atoms, an alkynyl group of 2 to 10 carbon atoms, a cycloalkyl group of 3 to 10 carbon atoms, an aryl group of 6 to 10 carbon atoms, a heteroalkyl group of 1 to 10 carbon atoms, a heteroalkenyl group of 2 to 10 carbon atoms, a heteroalkynyl group of 2 to 10 carbon atoms, a heterocycloalkyl group of 3 to 10 carbon atoms, or a heteroaryl group of 3 to 10 carbon atoms, where $R_1$, $R_2$, and N, to which $R_1$ and $R_2$ are attached, are optionally combined with each other to form an aliphatic hetero hydrocarbon ring of 5 to 20 carbon atoms or an aromatic hetero hydrocarbon ring of 6 to 20 carbon atoms, $R_7$, $R_8$, and X, to which $R_7$ and $R_8$ are attached, are optionally combined with each other to form an aliphatic hetero hydrocarbon ring of 5 to 20 carbon atoms or an aromatic hetero hydrocarbon ring of 6 to 20 carbon atoms, and each of $R_1$, $R_2$, $R_5$, $R_7$ and $R_8$ is unsubstituted or substituted with a substituent comprising one or more heteroatoms selected from N, O or S atoms, $R_3$, $R_4$ and $R_6$ are each independently an alkylene group of 1 to 10 carbon atoms, which is unsubstituted or substituted with an alkyl group of 1 to 10 carbon atoms, a cycloalkyl group of 5 to 10 carbon atoms, an aryl group of 6 to 10 carbon atoms, a heteroatom selected from N or O atoms or a substituent comprising the heteroatom, and X and Z are each independently one selected from N, O or S atoms, where if X is O or S, $R_8$ is not present, and if Z is O or S, Rs is not present.

3. The modification polymerization initiator of claim 2, wherein $R_1$, $R_2$, $R_5$, $R_7$ and $R_8$ are each independently an alkyl group of 1 to 10 carbon atoms or a heteroalkyl group of 1 to 10 carbon atoms, which is unsubstituted or substituted with a substituent comprising one or more heteroatoms selected from N, O or S atoms, where $R_1$, $R_2$, and N, to which $R_1$ and $R_2$ are attached, are optionally combined with each other to form an aliphatic hetero hydrocarbon ring of 5 to 10 carbon atoms or an aromatic hetero hydrocarbon ring of 6 to 10 carbon atoms, $R_7$, $R_8$, and X, to which $R_7$ and $R_8$ are attached, are optionally combined with each other to form an aliphatic hetero hydrocarbon ring of 5 to 10 carbon atoms or an aromatic hetero hydrocarbon ring of 6 to 10 carbon atoms, $R_3$, $R_4$ and $R_6$ are each independently an alkylene group of 1 to 10 carbon atoms, which is unsubstituted or substituted with an alkyl group of 1 to 6 carbon atoms, $R_5$ is an alkyl group of 1 to 10 carbon atoms, and X and Z are one selected from N, O or S atoms, where if X is O or S, $R_8$ is not present, and if Z is O or S, $R_5$ is not present.

4. The modification polymerization initiator of claim 1, wherein the compound represented by Formula 1 is a compound represented by the following Formula 1-1 to Formula 1-11:

[Formula 1-1]

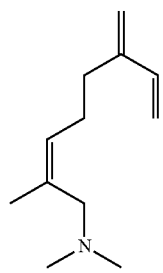

[Formula 1-2]

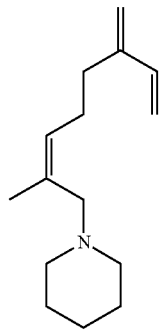

[Formula 1-3]

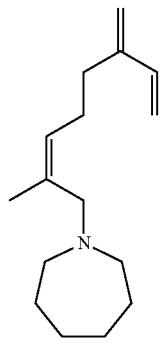

[Formula 1-4]

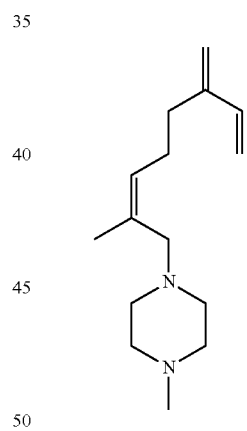

[Formula 1-5]

[Formula 1-6]

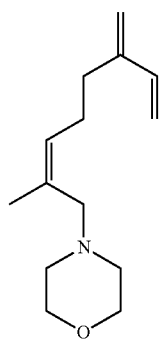

[Formula 1-7]
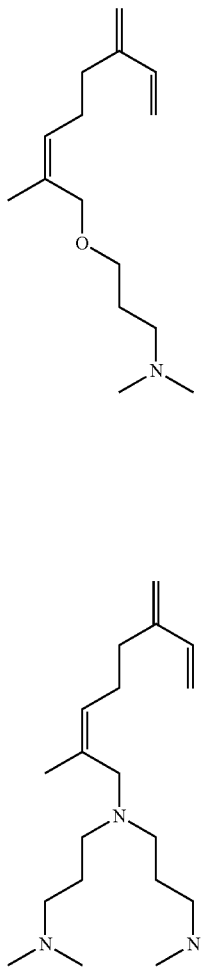

[Formula 1-8]
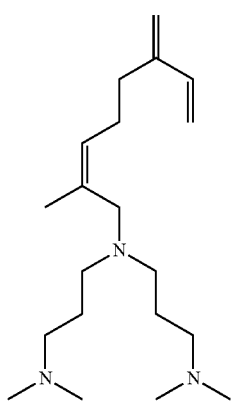

[Formula 1-9]
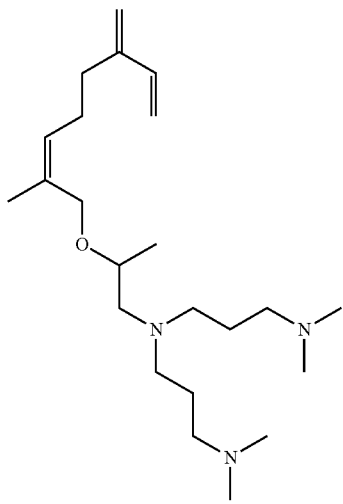

[Formula 1-10]
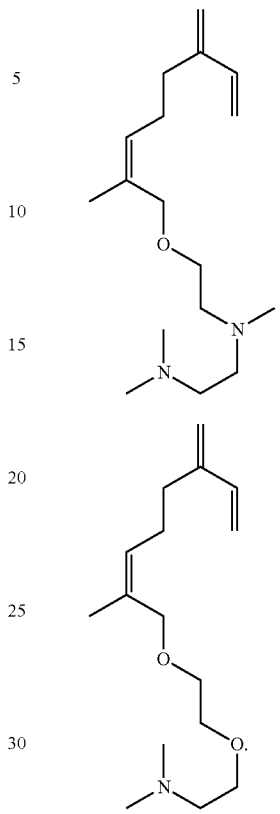

[Formula 1-11]
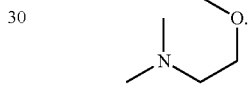

5. The modification polymerization initiator of claim 1, wherein in Formula 2, $R_e$ is hydrogen, an alkyl group of 1 to 10 carbon atoms, an alkenyl group of 2 to 10 carbon atoms, an alkynyl group of 2 to 10 carbon atoms, a cycloalkyl group of 5 to 10 carbon atoms or an aryl group of 6 to 10 carbon atoms.

6. The modification polymerization initiator of claim 1, wherein the at least one product comprises one or more selected from the group consisting of a compound represented by the following Formula 3, and isomers thereof, dimers thereof, trimers thereof, and oligomers thererof:

[Formula 3]
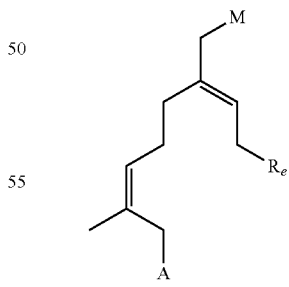

in Formula 3,
A is the same as defined in Formula 1,
M is Na, K or Li, and
$R_e$ is hydrogen or an alkyl group of 1 to 10 carbon atoms.

7. The modification polymerization initiator of claim 6, wherein the isomer comprises a compound represented by the following Formula 3-1, 3-2 or 3-3:

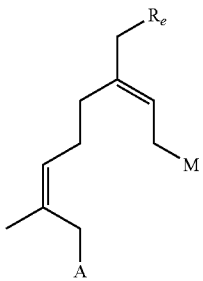

[Formula 3-1]

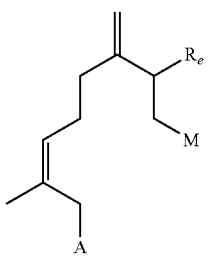

[Formula 3-2]

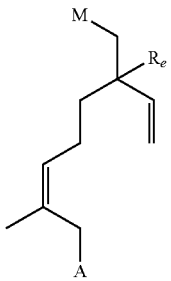

[Formula 3-3]

in Formula 3-1 to Formula 3-3,
A is the same as defined in Formula 1,
M is Na, K or Li, and
$R_e$ is hydrogen or an alkyl group of 1 to 10 carbon atoms.

8. A method for preparing the modification polymerization initiator of claim 1, the method comprising reacting a compound represented by the following Formula 1 and a compound represented by the following Formula 2:

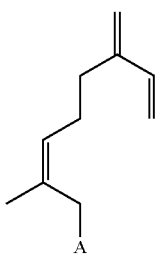

[Formula 1]

in Formula 1,
A is —$NR_aR_b$, —$OR_c$, or —$SR_d$, and
$R_a$ to $R_d$ are each independently an alkyl group of 1 to 30 carbon atoms, an alkenyl group of 2 to 30 carbon atoms, an alkynyl group of 2 to 30 carbon atoms, a cycloalkyl group of 3 to 30 carbon atoms, an aryl group of 6 to 30 carbon atoms, a heteroalkyl group of 1 to 30 carbon atoms, a heteroalkenyl group of 2 to 30 carbon atoms, a heteroalkynyl group of 2 to 30 carbon atoms, a heterocycloalkyl group of 2 to 30 carbon atoms or a heteroaryl group of 3 to 30 carbon atoms, where each of $R_a$ to Rd is unsubstituted or substituted with a substituent comprising one or more heteroatoms selected from N, O, S, Si or F atoms, and $R_a$, $R_b$, and N, to which $R_a$ and $R_b$ are attached, are optionally combined with each other to form a heterocycle of 3 to 20 carbon atoms, which is unsubstituted or substituted with an alkyl group of 1 to 30 carbon atoms, $$M-R_e \qquad \text{[Formula 2]}$$

in Formula 2,
M is an alkali metal, and
$R_e$ is hydrogen, an alkyl group of 1 to 30 carbon atoms, an alkenyl group of 2 to 30 carbon atoms, an alkynyl group of 2 to 30 carbon atoms, a cycloalkyl group of 5 to 30 carbon atoms, or an aryl group of 6 to 30 carbon atoms.

9. The method for preparing the modification polymerization initiator of claim 8, wherein
the reaction of the compound represented by Formula 1 and the compound represented by Formula 2 is performed in a continuous type reactor comprising a first channel and a second channel, and
prior to performing the reaction, a first reactant comprising the compound represented by Formula 1 is injected through the first channel to the continuous type reactor, and a second reactant comprising the compound represented by Formula 2 is injected through the second channel to the continuous type reactor.

10. The method for preparing the modification polymerization initiator of claim 9, wherein the first reactant is injected through the first channel in a rate of 1.0 g/min to 20.0 g/min into the continuous type reactor, and the second reactant is injected through the second channel in a rate of 1.0 g/min to 20.0 g/min into the continuous type reactor.

11. The method for preparing the modification polymerization initiator of claim 8, wherein the compound represented by Formula 1 and the compound represented by Formula 2 are reacted in a molar ratio of 1:0.5 to 5.

12. The method for preparing the modification polymerization initiator of claim 8, wherein the reaction is performed in a temperature range of 0° C. to 80° C. and pressure conditions of 0.5 bar to 10 bar.

13. The method for preparing the modification polymerization initiator of claim 8, wherein
the reaction is performed in the presence of a polar additive, and
the polar additive comprises one or more selected from the group consisting of tetrahydrofuran, ditetrahydrofurylpropane, diethyl ether, cycloamyl ether, dipropyl ether, ethylene dimethyl ether, ethylene diethyl ether, diethyl glycol, dimethyl glycol, tert-butoxyethoxyethane, bis(3-dimethylamino ethyl) ether, (dimethylamino ethyl) ethyl ether, trimethylamine, triethylamine, tripropylamine and tetramethylethylenediamine.

14. A modified conjugated diene-based polymer, comprising:
a repeating unit derived from a conjugated diene-based monomer; and
a functional group derived from the modification polymerization initiator of claim 1.

* * * * *